United States Patent [19]

Konopka

[11] Patent Number: 4,723,947
[45] Date of Patent: Feb. 9, 1988

[54] INSULIN COMPATIBLE INFUSION SET

[75] Inventor: April A. Konopka, San Dimas, Calif.

[73] Assignee: Pacesetter Infusion, Ltd., Sylmar, Calif.

[21] Appl. No.: 849,926

[22] Filed: Apr. 9, 1986

[51] Int. Cl.$^4$ .............................................. A61M 5/00
[52] U.S. Cl. .................................... 604/272; 604/282; 604/283; 156/294
[58] Field of Search ............... 604/282, 280, 283, 272; 156/294

[56] References Cited

U.S. PATENT DOCUMENTS

| | | | |
|---|---|---|---|
| 2,665,689 | 1/1954 | Butler | 604/272 |
| 2,725,058 | 11/1955 | Rathkey | 604/272 X |
| 4,627,844 | 12/1986 | Schmitt | 604/280 X |
| 4,636,346 | 1/1987 | Gold et al. | 604/280 |

Primary Examiner—Stephen C. Pellegrino
Attorney, Agent, or Firm—Leslie S. Miller

[57] ABSTRACT

An injection set for use with an external infusion source of fluid such as insulin is disclosed which injection set is constructed using multiwall tubing. The interior of the multiwall tubing is made of a material which is completely insulin compatible, while the exterior of the multiwall tubing is made of a material which may be solvent bonded. The multiwall tubing facilitates solvent bonding installation of an insert molded needle assembly and a connector to the ends of the tubing without necessitating the use of and incurring the disadvantages of epoxy bonding.

16 Claims, 5 Drawing Figures

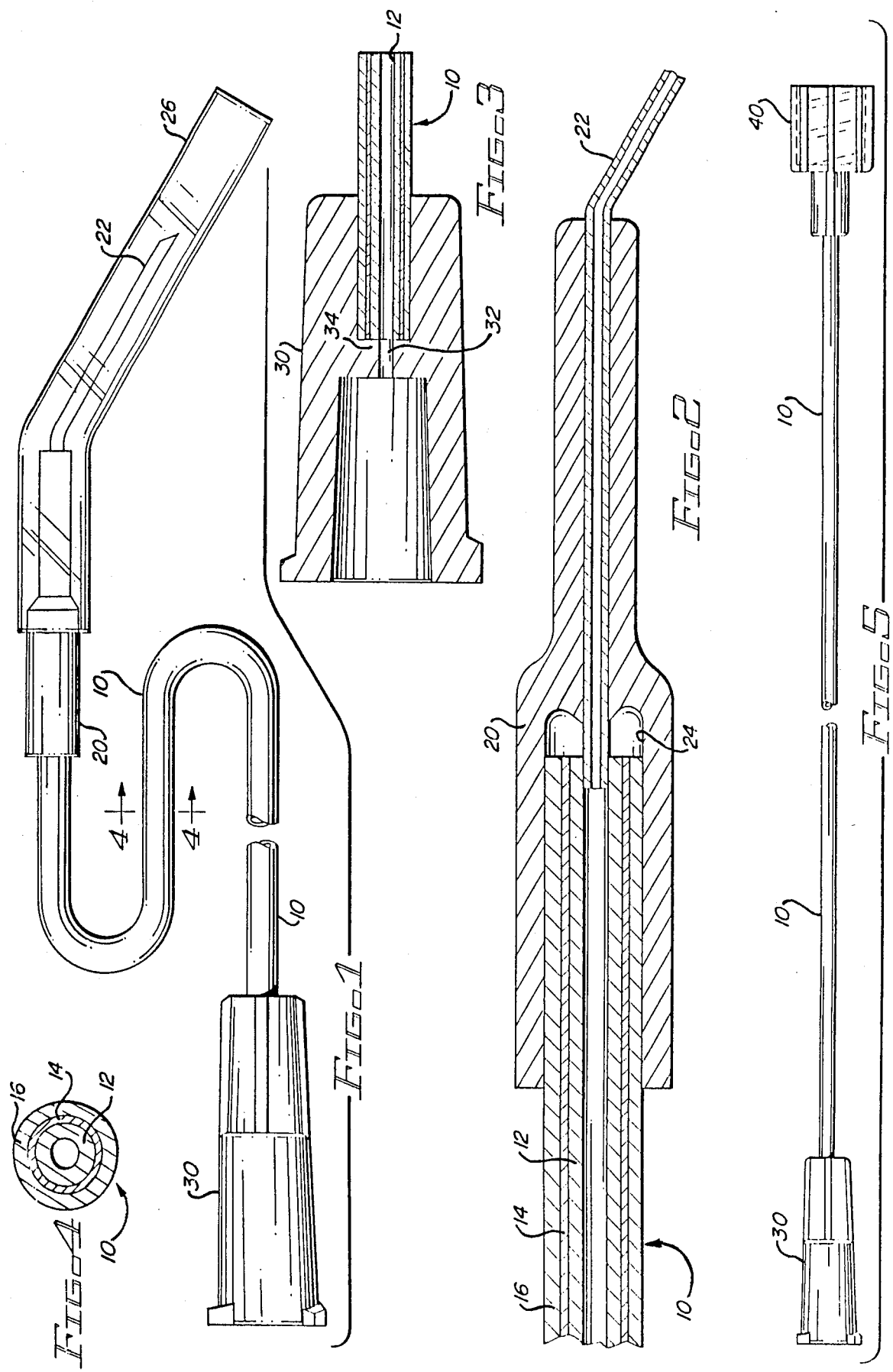

INSULIN COMPATIBLE INFUSION SET

BACKGROUND OF THE INVENTION

1. Field of the Invention

The present invention relates generally to injection devices for use with an external infusion system whereby a desired fluid is subcutaneously delivered to a patient, and more particularly to a disposable injection set for delivering insulin to the patient which injection set is conveniently and inexpensively manufactured of materials which will not cause a reaction with insulin passing therethrough, thereby avoiding the adverse results of such an insulin reaction.

Generally, in order to subcutaneously dispense a fluid from an external source to a patient, the distal end of a hollow needle is inserted through the skin of the patient, thereby providing a passageway to the desired subcutaneous injection location under the skin of the patient. The proximal end of the hollow needle located externally of the skin of the patient is connected to one end of a tube, the other end of which is connected to the external source of the fluid to be injected, typically with a luer connector made of hard PVC (polyvinyl chloride) and which may be easily connected by merely inserting the mating connectors together and twisting to lock them together.

A preferred technique for connecting the tube to the needle involves the molding of a hard PVC segment around the proximal end of the needle, and then utilizing flexible PVC tubing which may be solvent bonded to the hard PVC segment molded around the proximal end of the needle. Solvent bonding is preferred because of the relative ease of the solvent bonding operation, the strength and durability of the solvent bond, and the inexpensive cost of solvent bonding. Since such infusion sets are disposable, cost and acceptable shelf life are important criteria by which such an infusion set will be judged.

The recent popularity of insulin infusion pumps as an alternative to multiple daily injections for insulin-dependent diabetics requires the use of such an injection set to deliver insulin from a small, portable insulin infusion pump to the subcutaneous injection location. It has been determined that there exists a substantial problem with the use of injection sets as described above in that flexible PVC is not completely insulin compatible. This is in contrast to hard PVC, which is perfectly safe for use with insulin. While the exact nature of the reaction exhibited by insulin in contact with flexible PVC has not been determined with certainty, it is believed that the insulin, which is pH sensitive, reacts with $CO_2$, the flow of which therethrough is not inhibited by flexible PVC. In addition, the large quantities of plasticizer used in flexible PVC may result in a leaching problem when used with insulin.

Since flexible PVC is not a barrier for $CO_2$, the $CO_2$ which flows through the flexible PVC tubing will react with the insulin, causing the insulin to aggregate and to precipitate out of solution. Such precipitation of the insulin will likely cause clotting and blockage in the tube or in the needle, thereby inhibiting the flow of insulin to the subcutaneous depot.

Heat will also accelerate the clotting process of insulin in flexible PVC tubing without the pH change caused by $CO_2$. The reason for this has not been finally determined, but it may be due to zinc in the insulin forming zinc chloride. In any event, heat will further compound the situation faced by delivery of insulin through flexible PVC tubing.

The amount of insulin exiting the injection set will therefore vary considerably, with portions of the insulin becoming attached to the interior of the tube and eventually coating the interior of the tube even if blockage does not occur. Over time, the situation will improve somewhat assuming blockage of the tube per se does not occur, but the amount of insulin actually delivered to the patient will vary considerable even with the best of circumstances. It may therefore be appreciated that the use of a flexible PVC tubing injection set to deliver insulin from an insulin infusion pump is neither desirable nor medically acceptable.

It should also be noted that other substances exhibit reactions when delivered through flexible PVC tubing. Lipids and proteins have adverse reactions with flexible PVC delivery systems, and nitroglycerin also reacts to some degree with a flexible PVC environment.

One solution which has been discovered to the problem has been through the use of polyethylene tubing, which does not cause a reaction with insulin passing therethrough. Polyethylene is a barrier to $CO_2$, and the major problem of $CO_2$ passing through the tubing is thereby eliminated. Additionally, the problem of clotting of the insulin due to heat is also substantially minimized.

However, polyethylene is not solvent bondable as is flexible PVC, and a substantial problem in manufacturing of injection sets using polyethylene has arisen. The preferred method to date has been to use epoxy to "pot" the polyethylene tubing to the needle, without using a hard PVC segment molded onto the needle. Although the hard PVC segment could be used, since polyethylene is not susceptible to solvent bonding it would be necessary to epoxy the polyethylene tubing to the hard PVC segment, resulting in a higher cost injection set.

Several problems have arisen with the use of epoxy bonded polyethylene infusion sets, all of which are due to the relative disadvantage of the epoxy bonding process to the solvent bonding process. First of all, an epoxy bond is simply not as strong as a solvent bond. Secondly, epoxy bonds have substantial aging problems, which limit shelf life of the injection set. Since the epoxy bond loses its mechanical bonding properties over time, the injection set will become less sturdy, with the potential for the tubing coming loose from the needle increasing substantially over time. Thirdly, batch control of epoxy used in epoxy bonding is time consuming and cumbersome. Finally, epoxy bonding or "potting" is a more expensive process than solvent bonding, resulting in a product having an economic disadvantage relative to a product made by solvent bonding.

It is thereby apparent that there exists a substantial need for an injection set for delivery of insulin (or other fluids exhibiting reactions when flowed through flexible PVC tubing), which injection set utilizes polyethylene tubing to inhibit reaction and subsequent degradation of insulin flowing therethrough. It is a primary objective that the injection set be susceptible to manufacture by solvent bonding, thereby resulting in a superior mechanical bond having great strength and excellent shelf life.

It is also desirable that the improved injection set be of economical manufacture, to thereby result in an inexpensive disposable product which may be easily marketed. Finally, it is desirable that the improved injection set achieve the aforementioned advantages and solve the previously mentioned disadvantages without substantial disadvantage.

SUMMARY OF THE INVENTION

The disadvantages and limitations of the background art discussed above are overcome by the present invention. With this invention, multiwall tubing such as coextruded or triextruded tubing having polyethylene as the inner layer and flexible PVC as the outer layer is used to advantageously construct an injection set. The needle is made by using insert molded technology, with a hard PVC segment molded around the proximal end of the needle. One end of the coextruded or triextruded tubing is inserted into the hard PVC segment with the inner polyethylene tubing layer around the proximal end of the needle, and the outer flexible PVC layer is solvent bonded to the hard PVC segment.

The other end of the coextruded or triextruded tubing is solvent bonded to a hard PVC connector, typically a luer connector. In the coextruded tubing, the outer layer of flexible flexible PVC tubing is extruded over an inner layer of polyethylene. Triextruded tubing, which is used in the preferred embodiment, has a middle layer which bonds to both flexible PVC and polyethylene, and the bond achieved between the layers is better than the bond between flexible PVC and polyethylene in the coextruded tubing.

Since the inner layer of the multiwall tubing is polyethylene, the injection set of the present invention is suitable for use with insulin and other fluids exhibiting a reaction when flowed through flexible PVC tubing. Since the outer layer of the multiwall tubing is flexible PVC, solvent bonding may be utilized in the construction of the injection set, thereby resulting in a product having excellent strength and shelf life characteristics while being of economical manufacture. It may therefore be appreciated that the present invention results in a product having substantial advantages over the background art, while presenting no disadvantage whatsoever.

DESCRIPTION OF THE DRAWINGS

These and other advantages of the present invention are best understood with reference to the drawings, in which:

FIG. 1 is a plan view of an injection set constructed according to the teachings of the present invention;

FIG. 2 is a sectional view of the needle end of the injection set of FIG. 1, illustrating the connection of triextruded tubing to a hard PVC segment insert molded onto the proximal end of a needle;

FIG. 3 is a sectional view of the female connector end of the injection set shown in FIG. 1, illustrating the connection of triextruded tubing to a hard PVC female luer connector;

FIG. 4 is a cross sectional view of the triextruded tubing used in the preferred embodiment; and FIG. 5 is a plan view of an extension set constructed according to the teachings of the present invention.

DETAILED DESCRIPTION OF THE PREFERRED EMBODIMENT

The preferred embodiment is illustrated in FIGS. 1-3, and is constructed using multiwall tubing having as an annular inner layer polyethylene and as an annular outer layer flexible PVC. Multiwall tubing is generally manufactured by extruding the inner or innermost tubing first, and successively extruding one or more additional annular layers around the previously extruded layer or layers.

The present invention requires at least a coextruded tubing, which is a two layer tubing, with the inner layer being polyethylene and the outer layer being flexible PVC. Practice has shown that coextruded tubing has a propensity to separate somewhat under certain conditions, and this separation may allow backwashing of insulin to occur into the space between the inner and outer layers of tubing. Such a phenomenon would result in a shortage of insulin in the supply stream to the patient, and the difficulty in fabrication of a stable coextruded tubing of the desired inner and outer materials makes the coextruded tubing less desirable from both reliability and performance standpoints. Therefore, in the preferred embodiment of the present invention a triextruded multiwall tubing is utilized.

A segment of triextruded multiwall tubing 10 is shown in FIG. 1, and in sectional view in FIGS. 2 and 3, and in cross section in FIG. 4. The triextruded tubing 10 has as its innermost layer an annular polyethylene tubing layer 12, which polyethylene tubing 12 would be extruded first. In the preferred embodiment, the polyethylene tubing 12 has an inner diameter of 0.01–0.025 inches, and a thickness of 0.005–0.012 inches, preferably 0.007–0.009 inches.

An intermediate layer 14 is extruded around the inner tubing layer 12, which intermediate layer 14 is made of a material which will have good adhesion qualities to both polyethylene and to flexible PVC. In the preferred embodiment, the intermediate layer is a member of the polyethylene family having superior adhesion characteristics to both polyethylene and to flexible PVC, such as EVA (ethylene-vinyl acetate). The intermediate layer 14 is relatively thin, on the order of 0.0005–0.005 inches, and preferable 0.001–0.002 inches.

An outer layer 16 is extruded over the intermediate layer 14 and the inner layer 12, and this outer layer 16 is a flexible PVC. The thickness of the outer layer 16 is between 0.005 and 0.015 inches, preferably 0.010–0.012 inches. In the preferred embodiment, the completed triextruded tubing 10 will have an outside diameter of approximately 0.06 inches.

It may be appreciated that the triextruded tubing 10 will have the best of both worlds, namely that its inner diameter is polyethylene and is therefore a desirable conduit for insulin, while its outer diameter is flexible PVC, and is therefore able to be conveniently solvent bonded.

Referring again to FIGS. 1 and 2, a hard PVC segment 20 is insert molded around the area adjacent to the proximal or external end of a 27 Gauge pre-bent hollow needle 22. It is important to note that the proximal end of the needle 22 is located in a cylindrical cavity 24 in the hard PVC segment 20, which cavity 24 is open at the end of the hard PVC segment 20 opposite the end from which the internal or distal end of the needle 22 extends. Except for the fact that the proximal end of the needle 22 is within the cylindrical cavity 24 and not covered by the hard PVC segment 20, the configuration of the hard PVC segment 20 and the needle 22 is not unlike that known in the art. In fact, the technique of insert molding a hard PVC segment onto a needle is well known in the art.

One end of the triextruded tubing 10 is inserted into the cylindrical cavity 24, which is sized to receive the outer diameter of the tubing 10. It will be appreciated that the outer flexible PVC 16 layer of the tubing 10 is adjacent the cylindrical cavity 24 of the hard PVC segment 20. The inner diameter of the inner polyethylene tubing layer 12 extends over the proximal end of the hollow needle 22 in sealing fashion to prevent the insulin from seeping out and into contact with the outer flexible PVC layer 16.

The outer flexible PVC layer 16 is bonded to the portions of the cylindrical cavity 24 it contacts by solvent bonding in the preferred embodiment. A 100% reagent solvent such as cyclohexanone is used to form a strong, durable seal with excellent shelf life characteristics in an economical, highly repeatable operation. It may also be noted in FIG. 1 that a flexible needle guard 26 is removably installed over the needle 22 and a portion of the segment 20.

Referring now to FIG. 3, the other end of the triextruded tubing 10 is inserted into one end of a female luer connector 30 made of hard PVC. The female luer connector 30 has an aperture 32 therethrough which allows fluid communication between the connector 30 and the interior of the inner polyethylene tubing layer 12. The joint between the tubing 10 and the connector is sealed with solvent in a manner similar to that described above. The tubing 10 is inserted into the connector 30 so the butt end of the tubing 10 is sealed against a flange portion 34 of the connector 30, with the aperture 32 aligned with the center of the inner tubing 12, thereby preventing insulin passing through the connector 30 and the tubing 10 from coming into contact with the flexible PVC outer layer 16.

It will be appreciated that while FIGS. 1-3 illustrate an infusion set, the principles of construction of the present invention are equally applicable to a variety of similar devices, such as the extension illustrated in FIG. 5. A female luer connector 30 is mounted on one end of the triextruded tubing 10, and a male luer connector 40 is mounted on the other end of the tubing 10.

Similarly, although the present discussion pertains primarily to an insulin injection set, the teachings of the present invention are equally applicable to devices for use with other liquids which are sensitive to flexible PVC, such as lipids and proteins, as mentioned above.

It will be understood that the present invention provides for transfer of insulin from an external infusion pump or the like to a subcutaneous infusion depot. Since the interior of the tubing of the injection set now uses polyethylene, the problem of blockage and clotting of insulin in the device is virtually eliminated. Neither $CO_2$ nor heat will have the adverse effects mentioned previously on insulin supplied through the polyethylene inner tubing of the present invention.

Additionally, since the outer surface of the tubing is flexible PVC, the assembly of the injection set may be made using solvent bonding. This makes the mechanical integrity of the injection set substantially better than injection sets assembled using epoxy bonding. The injection set of the present invention also has a superior shelf life, and the economical construction utilizing bonding gives it a highly desirable competitive advantage over similar devices for insulin use made using epoxy bonding of polyethylene.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. An injection set for use with an external infusion system to deliver a desired fluid to a subcutaneous injection location under the skin of a patient, comprising:
   a segment of flexible tubing having a first end and a second end, said tubing being open on said first and second ends and having a passage therethrough communicating with said first and second ends, said tubing being of multiwall construction and having an inner annular layer defining said passage, said inner annular layer being made of a first material which is compatible with said desired fluid, said tubing also having an outer annular layer which is flexible and solvent bondable;
   a connector for facilitating fluid communication with said first end of said tubing, said connector being mechanically connected to said first end of said tubing to supply said desired fluid from said external infusion system to said passage in said tubing;
   a needle having a proximal end and a distal end, said needle for insertion by the distal end thereof into said subcutaneous injection location under the skin of said patient; and
   a segment which is insert molded onto the proximal end of said needle, the distal end of said needle extending from one end of said segment, said segment having an essentially cylindrical cavity therein in which said proximal end of said needle is located, said cylindrical cavity having an opening therein at the other end of said segment, said second end of said tubing being inserted into said cylindrical cavity in a manner whereby said said inner layer of said tubing at said second end of said tubing is inserted over a portion of said proximal end of said needle with the proximal end of said needle being in fluid communication with said passage in said tubing, and the inner portion of said cylindrical cavity of said segment being mechanically connected to said outer layer of said tubing at said second end of said tubing.

2. An injection set as defined in claim 1, wherein said inner layer of said tubing is made of polyethylene and said outer layer of said tubing is made of flexible PVC.

3. An injection set as defined in claim 1, wherein said tubing has an intermediate layer disposed between said inner layer and said outer layer.

4. An injection set as defined in claim 3, wherein said inner layer is made of polyethylene and said outer layer is made of flexible PVC, said intermediate layer being made of a material which has good adhesion qualities to both polyethylene and flexible PVC.

5. An injection set as defined in claim 4, wherein said intermediate layer is made of EVA.

6. An injection set as defined in claim 3, wherein said inner layer has an inner diameter of 0.01-0.025 inches and a thickness of 0.005-0.012 inches, said intermediate layer has a thickness of 0.0005-0.005 inches, and said outer layer has a thickness of 0.005-0.015 inches.

7. An injection set as defined in claim 1, wherein said segment is made of hard PVC.

8. An injection set as defined in claim 1, wherein said tubing is mechanically connected to said connector and to said segment by solvent bonding.

9. An injection set as defined by claim 8, wherein said solvent bonding is done with a solvent which solvent is a 100% reagent solvent.

10. An injection set as defined in claim 9, wherein said solvent is cyclohexanone.

11. An injection set as defined in claim 1, wherein said connector includes disposed therein a flange having an aperture therethrough, said first end of said tubing being mounted in said connector in abutting relationship with said flange, said aperture in said flange being aligned with the center of said inner layer of said tubing and in fluid communication with said passage.

12. An injection set as defined in claim 11, wherein said desired fluid is insulin.

13. An injection set as defined in claim 1, wherein said connector is a female luer connector.

14. An injection set for use with an external drug infusion pump to deliver insulin supplied by said pump to a subcutaneous injection location under the skin of a patient, comprising:
   a segment of said triextruded flexible tubing having a first end and a second end, said tubing being open on said first and second ends, said tubing having an inner annular layer defining a passage therethrough between said first and second ends, said inner annular layer being made of a polyethylene, said tubing having an intermediate annular layer around said inner layer, said intermediate layer being made of EVA, said tubing also having an outer annular layer, said outer layer being made of flexible PVC,
   a female luer connector for connection with said first end of said tubing, said connector being made of hard PVC, said connector being solvent bonded to said outer layer of said tubing to supply said desired fluid from said external infusion system to said passage in said tubing;
   a needle for insertion by the distal end thereof into said subcutaneous injection location under the skin of said patient; and
   a hard PVC segment which is insert molded onto said needle near the proximal end thereof, said segment having a cylindrical cavity therein in which said proximal end of said needle is located, said cylindrical cavity having an opening therein, said second end of said tubing being inserted into said cylindrical cavity in a manner whereby the proximal end of said needle is located inside of the portion of said inner layer of said tubing at said second end thereof, said needle being in fluid communication with said passage in said tubing, the inner portion of said cylindrical cavity of said segment being solvent bonded to said outer layer of said tubing at said second end thereof.

15. An injection set comprising:
   a length of multiwall tubing having an inner annular layer of polyethylene and an outer annular layer of flexible PVC, said tubing having a passage therethrough;
   a hollow needle having a distal end and a proximal end;
   a segment of hard PVC mounted around the proximal end of said hollow needle, said segment having a cavity therein into which one end of said tubing is inserted, the outer layer of said tubing being solvent bonded to the interior of said cavity with said inner layer of polyethylene at said one end of said tubing being located over the proximal end of said needle, said passage being in fluid communication with said proximal end of said needle; and
   a hard PVC connector solvent bonded to the other end of said tubing, said passage also being in fluid communication with the interior of said connector.

16. A method of making an injection set, comprising:
   providing a length of multiwall tubing having an inner annular layer of polyethylene and an outer annular layer of flexible PVC, said tubing having a passage therethrough;
   insert molding a segment of hard PVC around the proximal end of a hollow needle;
   inserting one end of said tubing into a cavity in said segment, the outer layer of said tubing being solvent bonded to the interior of said cavity with said passage being in fluid communication with said proximal end of said needle; and
   solvent bonding the other end of said tubing to a hard PVC connector, said passage also being in fluid communication with the interior of said connector.

* * * * *